United States Patent [19]
Komissarova et al.

[11] Patent Number: 5,559,152
[45] Date of Patent: Sep. 24, 1996

[54] PHARMACEUTICAL COMPOSITION HAVING ANTIACOHOLIC ACTIVITY

[76] Inventors: Irina A. Komissarova, ulitsa Medikov, 24, kv. 47; Julia V. Gudkova, ulitsa Berzarina, 9, kv. 94; Tatyana D. Soldatenkova, Pokrovsky bulvar, 14/5, kv. 73, all of Moscow; Natalya M. Burbenskaya, Ozersky raion, selo Sennitsy, Moscowskaya oblast; Tatyana T. Kondrashova, ulitsa Severodvinskaya, 9, kv. 305; Irina L. Kalantar, ulitsa Festivalnaya, 28, kv. 66, both of Moscow, all of Russian Federation; Jury M. Toropov, ulitsa Moldybaeva, 28, kv. 24, Beshkek, Kyrgyzstan; Galina F. Semenova, ulitsa Perekopskaya, 11, kv. 43, Moscow, Russian Federation; Rjurik P. Nartsissov, ulitsa Medikov, 24, kv. 47, Moscow, Russian Federation; Elena V. Kalinina, ulitsa Teply Stan, 15, kv. 14, Moscow, Russian Federation

[21] Appl. No.: 204,163
[22] PCT Filed: Jul. 6, 1992
[86] PCT No.: PCT/RU92/00134
  § 371 Date: May 24, 1994
  § 102(e) Date: May 24, 1994
[87] PCT Pub. No.: WO94/01099
  PCT Pub. Date: Jan. 20, 1994
[51] Int. Cl.⁶ ..................................... A61K 31/19
[52] U.S. Cl. .................. 514/557; 514/810; 514/811
[58] Field of Search ................... 514/557, 810, 514/811

[56] References Cited
FOREIGN PATENT DOCUMENTS

| | | |
|---|---|---|
| 0363337 | 4/1990 | European Pat. Off. . |
| 3111770 | 10/1982 | Germany . |
| 3641495 | 7/1991 | Germany . |
| 1090405 | 5/1984 | U.S.S.R. . |
| 2198041 | 6/1988 | United Kingdom . |

OTHER PUBLICATIONS

Ronai, E. et al. "The Inhibitory Effect . . . " Int. J. Radiat, Bio., 1987 vol. 51, No. 4611617 pp. 3611–3617.
Ivnitski, Y. Y. et al. "Protection of Mice. . . " Radiobiology, Academy of Science of USSR, vol. 30, 5 ed., 1990, pp. 704–706.
Freidman, S. L. et al. "Comparison of Effect. . . " Succinic Acid Therapeutic Effect, Academy of Science of the USSR, 1976, pp. 49–55, pp. 106–110.
Mochizuki et al., "Intoxication–free alcohol beverages", Chemical Abstracts 108:93106, 1990.

*Primary Examiner*—Kevin E. Weddington
*Attorney, Agent, or Firm*—Ladas & Parry

[57] ABSTRACT

A pharmaceutical composition having antialcoholic activity, stimulating energy metabolism and acid-forming and secretory functions of stomach mucosa, having radioprotective and anticholera activities contains a mixture of succinic acid and citric acid or pharmaceutically acceptable salts thereof as an active ingredient.

A method for preventing and treating alcohol intoxication and alcohol abstinence syndrome, stimulating energy metabolism stimulating and diagnosing acid-forming and secretory functions of stomach mucosa, protecting against radiation damage and preventing cholera which comprises oral administration of an effective amount of the present composition.

9 Claims, 2 Drawing Sheets

PHARMACEUTICAL COMPOSITION HAVING ANTIACOHOLIC ACTIVITY

This application is a 371 of PCT/RU92/00134 filed Jul. 6, 1992.

FIELD OF THE INVENTION

The present invention relates to medicine, in particular to a new drug having antialcoholic activity, stimulating energy metabolism and acid-forming and secretory functions of stomach mucosa, having radioprotective and anticholera activities.

BACKGROUND OF THE INVENTION

Known is alco-zelzer which is a widely used antialcoholic drug containing citric acid and having antitoxic activity; said drug is administered during the periods of acute alcoholic intoxication. Nevertheless alco-zelzer may be administered only occasionally to treat alcohol intoxication at home. Long-term chronic application of alco-zelzer to provide regular detoxication of alcohol addicted patients causes serious complications due to the presence of aspirin; such complications include dyspepsia, pathogenic changes in stomach mucosa, disfunctioning of nervous system and hemocoagulation. Besides alco-zelzer fails to reduce alcohol dependence and shows no alcoprotective activity, i.e. said drug cannot be used to prevent alcohol intoxication.

Known is an antialcoholic composition based on biological materials comprising citric and succinic acids as well as more than 80 different natural components (GB 2 198 041, DE 3 641 495). Said composition used as an additive for alcoholic drinks and beverages has antitoxic activity and reduces alcohol dependence, nevertheless it shows no alcoprotective effect, its manufacturing is expensive and has limited sources of raw materials, moreover standard norms can hardly be set for such a composition.

Alcoholism is known to be accompanied by worsened appetite which is one of the main symptoms of the disease appearing as a result of lessened acid-forming and secretory function of stomach mucosa, as well as by asthenia.

Known is a method for stimulating energy metabolism and hydrochloric acid secretion by stomach mucosa by using succinic acid ("Terepevticheskoje dejstvie jantarnof kisloty") (Therapeutic Effect of Succinic Acid), the USSR Academy of Sciences, collected articles, 1976, Puschino, pp. 49–55; pp. 106–107). Nevertheless said effects are unstable and accompanied by lessened functional activity.

The diagnostics of acid-forming and secretory function of stomach widely employs such drugs as histamine and pentahistamine. The use of histamine is nevertheless limited due to frequent complications such as nettle-rash, larynx edema, anaphylactic shock. Pentahistamine administration causes sialorrhea, nausea, stomach pains, hypotensia, followed by lessening of acid-forming and secretory function of stomach, as well as worsened appetite.

Presently different antibiotics and vaccines are used to prevent cholera. But antibiotics are toxic, have low-effectiveness and their administration fails to limit the spreading of cholera. The administration of vaccines often causes allergic and toxic complications, the use of said vaccines is limited due to a relatively long period of formation of specific immunity as well as due to a relatively short period of effective protection. Therefore when an endemic center of cholera emerges these vaccines appear to give an unsatisfactory effect.

Known is a wide range of radioprotectors represented by compounds of different classes. But said compounds are toxic and have to be used in high dosages. In recent years much effect has been taken to find radioprotectors among natural metabolites. In particular, radioactive effect of succinic acid has been discovered, but the dosages needed to attain such effect are very high ("International Journal of Radiation Biology", 1987, No. 4, v. 51, Taylor & Francis, Great Britain, pp. 611–617; "Radiobiologia", 1990, No. 5, V. 30, Nauka Publishers, Moscow, pp. 704–706).

It should be noted that the present state of the art does not know absolutely safe drugs (badly needed in acute stages of alcoholism) which could show both alcohol-detoxifying and alcoprotective activities, reduce alcohol dependence, increase energy metabolism, acid-forming secretory function of stomach mucosa, improve appetite, as well as show radioprotective and anticholera activities.

DETAILED DESCRIPTION OF THE INVENTION

The present pharmaceutical composition is new. It has not been disclosed in the prior art.

The basic object of the invention is a highly effective non-toxic composition producing no side-effects and having alcohol-detoxifying and alcoprotective activities, reducing alcohol dependence and stimulating energy metabolism, acid-forming and secretory function of stomach mucosa, having radioprotective an anticholera activities.

The object of the invention is achieved by the claimed composition comprising an active ingredient and a pharmaceutical solvent. The active ingredient is a mixture of succinic acid and citric acid or pharmaceutically acceptable salts thereof.

The present pharmaceutical composition may be in the form of a powder, a solution or tablets. Preferably, the composition is used in the form of a solution or a powder, in the amount of 0.1–0.3 g of succinic acid and 0.025–0.085 g of citric acid or pharmaceutically acceptable salts thereof per one dose. Preferably the composition contains water or alkaline mineral water as a solvent.

The present pharmaceutical composition has highly effective alcohol-detoxifying and alcoprotective activities, reduces alcohol dependence and stimulates energy metabolism, acid-forming and secretory function of stomach mucosa, shows radioprotective and anticholera activities; said composition is used for preventing and treating acute alcohol intoxication and its after-effects, for treating astheno-vegetative disorders and for improving appetite during astenic period of alcohol withdrawal syndrome; in gastroenterological clinics it can be used as a diagnosticum for testing secretory activity of stomach mucosa; also it can be used to provide protection against radioactive damage and to prevent cholera.

BRIEF EXPLANATION OF THE DRAWINGS

The invention is further disclosed by the drawings, where.

THE MOST PREFERRED EMBODIMENT

Figure 1:
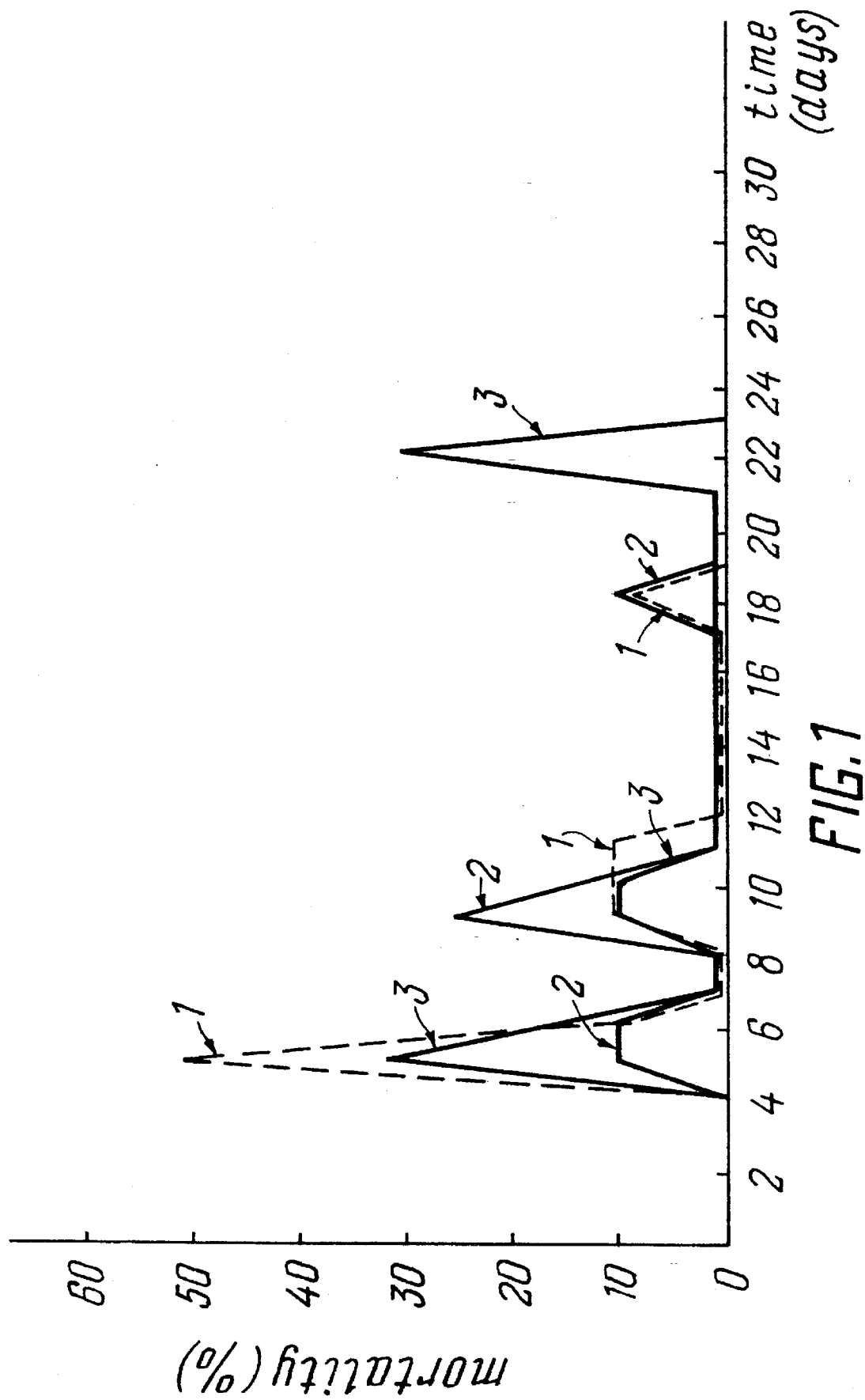
FIG. 1 shows the effect produced by the present composition and glutathione on the mortality of rats subjected to gamma-irradiation.

The present composition is a mixture of succinic acid and citric acid. Said carboxylic acids are natural metabolites being present in vegetable and animal tissues. In laboratory conditions they have the form of white odorless powders readily soluble in water and alkaline solutions and poorly soluble in ethyl alcohol and oils.

The present composition has been studied in the course of experiments using animals and in clinics using human patients.

Antialcohol activity of the present composition has been studied using male amphibians weighing 30–40 g each, mice weighing 20–25 g each and male rats weighing 200–250 g each.

Using a standard model (exposed hemispheres and olfactory nerves) of *Rana temporaria* frog a stimulation of olfactory nerve was carried out with the frequency of once per two minutes, and during 40–60 min, the induced potential of primordial hippocampus was registered. Registered was the amplitude of five basic components of the induced potential, i.e. the positive component ($PC_1$) showing the arrival of afferent volley and the emergence of afferent exitatory postsynaptic potentials, negative component (NC) related to the development of early inhibitory postsynaptic potentials, positive potential ($PC_2$) related to the development of primordial hippocampus of reverse exitatory postsynaptic potentials, and volley discharges in neurons, negative potential $NP_2$ characterizing later inhibitory postsynaptic potentials and later positive potential ($PC_{lt}$) related to depolarizational long-term potential of neurons.

Before the registration of induced potential the first group consisting of 10 animals was given (by i.m. injection) the present composition in the dosage of 3.5 mg/kg of animal weight 20 min. before the injection of 10% ethanol in the dosage of 0.5 g/kg of animal weight; to the second group consisting of 10 animals 20 min. before the injection of 10% ethanol in the same dosage, the same amount of saline was administered; to the control group consisting of 10 animals only a corresponding amount of saline was administered. The results are set out in Table 1.

Table 1 shows that with prior administration of the present composition, ethanol does not cause notable changes in the amplitude of the components of induced potential, which fact proves its alcoprotective detoxifying activity.

TABLE 1

The effect of the claimed composition on the amplitude of the components of induced potential of primordial hippocampus in frogs (in percent to control, $M \pm m$)

| Components of induced potential | Amplitude of the components of induced potential | |
| --- | --- | --- |
| | 1st group Claimed composition + ethanol | 2nd group Saline + ethanol |
| $PC_1$ | 92.35 ± 0.98* | 88.72 ± 0.17 |
| NC | 92.86 ± 7.15 | 86.86 ± 12.09 |
| $PC_2$ | 94.04 ± 0.71* | 49.87 ± 1.48 |
| $NP_2$ | 87.37 ± 11.18* | 79.53 ± 0.22 |
| $PC_{lt}$ | 78.79 ± 12.12* | 83.22 ± 1.40 |

Note:
Unabbreviated names of the components of induced potential are presented above.
x means that the difference from the 2nd group is true, $p < 0.05$.

The effect of the present composition on the development of acute alcohol intoxication in mice and rats has been studied. Test animals were given (intrastomach) the present composition in the dosage of 3.75 mg/kg of animal weight 20 min. before i.p. injection of ethanol in the dosage of 2; 3; 4.5 and 6 g/kg of animal weight; the control group was given the corresponding amount of water 20 min. before ethanol injection. The duration of onside position of animal was considered. The data obtained are shown in Table 2.

TABLE 2

The effect of the claimed composition on the duration of on-side position of mice and rats (in minutes, $M \pm m$)

| Groups of animals | Number of animals per group | Duration of side position | Truth of the tests, p |
| --- | --- | --- | --- |
| Mice | | | |
| Control: 10% ethanol (2 g/kg anim. wt) + water | | 23.6 ± 1.89 | |
| Test: 10% ethanol (2 g/kg anim. wt) + claimed composition | 10 | 4.5 ± 0.47 | <0.01 |
| Control: 10% ethanol (3 g/kg anim. wt) + water | | 34.0 ± 8.4 | |
| Test: 10% ethanol (3 g/kg anim. wt) + claimed composition | 10 | 13.0 ± 2.4 | <0.05 |
| Control: 25% ethanol (6 g/kg anim. wt) + water | | 100.0 ± 7.2 | |
| Test: 25% ethanol (6 g/kg anim. wt) + claimed composition | 10 | 39.0 ± 5.3 | <0.01 |
| Rats | | | |
| Control (shortsleeping) 25% ethanol (4.5 g/kg anim. wt) + water | | 77.0 ± 4.0 | <0.01 |
| Test (shortsleeping): 25% ethanol (4.5 g/kg anim. wt) + claimed composition | 10 | 38.0 ± 2.3 | |
| Control (longsleeping): 25% ethanol (4.5 g/kg anim. wt) + water | | 155.0 ± 13.0 | <0.05 |
| Test (longsleeping): 25% ethanol (4.5 g/kg anim. wt) + claimed composition | 10 | 70.0 ± 9.0 | |

Table 2 shows that prior administration of the claimed composition, while reducing the duration of on-side position 2–4 times, provides alcoprotective detoxifying effect irrespective of the animals sensitivity (shortsleeping and longsleeping rats) to ethanol.

The effect of the present composition on behavioral reactions of mice suffering acute alcohol intoxication has been studied. The first group of animals was given (intrastomach) the present composition in the dosage of 1.5 mg/kg animal weight 20 min. before i.p. injection of 10% ethanol in the dosage of 0.5 g/kg animal weight; the second group consisting of 40 animals 20 min. before i.p. injection of 10% ethanol in the same dosage was given (intrastomach) a corresponding amount of saline; in the control group consisting of 40 animals was given (intrastomach) only a corresponding amount of saline. Mice behavior was studied in the "open field" test. The results are shown in Table 3.

TABLE 3

The effect of the claimed composition on the behavior of mice suffering acute alcohol intoxication in "open field" test

| Behavioral parameters, $M \pm m$ | Groups of animals | | |
|---|---|---|---|
| | 1st Claimed composition + ethanol | 2nd Saline + ethanol | Control Saline |
| Simple transitions | $37.43 \pm 0.78^{x)}$ | $20.55 \pm 1.28^{xx)}$ | $43.00 \pm 0.71$ |
| "Light-darkness" transition | $16.40 \pm 0.88^{x)}$ | $12.35 \pm 1.01^{xx)}$ | $16.65 \pm 1.06$ |
| Dying out | $0.23 \pm 0.08^{x)}$ | $1.65 \pm 0.24^{xx)}$ | 0 |
| Sets | $40.73 \pm 2.55^{x)}$ | $15.30 \pm 1.08^{xx)}$ | $43.30 \pm 1.28$ |
| Grooming reaction | $1.03 \pm 0.22^{x)}$ | $1.32 \pm 0.17$ | $1.35 \pm 0.13$ |

$^{x)}$means that the difference from 2nd group is true, $p < 0.05$;
$^{xx)}$means that the difference from the control is true, $p < 0.05$.

Table 3 shows that with prior administration the present composition provides alcoprotective detoxifying effect reducing or preventing the changes in animal behavior caused by ethanol.

A comparative study of the effect of the present composition and that of succinic acid (which is one of the components of said composition) on acute alcohol intoxication in rats was carried out. The 1st group of animals was given (intrastomach) the present composition in the dosage of 1.85 mg/kg animal weight, the 2nd group of animals was given (intrastomach) succinic acid in the same dosage, the control group of rats was given (intrastomach) corresponding amount of water. 40 min. later all groups of animals were given i.p. injections of 25% ethanol in the dosage of 3.5 g/kg animal weight and the duration of their on-side position was registered. 60 min. after the animals have left on-side position, they were once against given injections of 25% ethanol in the dosage of 3 g/kg animal weight, and the duration of their on-side position was registered. The results of this study are shown in Table 4.

TABLE 4

The effect of the claimed composition and that of succinic acid on the duration of on-side position of rats after single and repeated ethanol injections

| | | Duration of on-side position, min. $M \mp m$ | |
|---|---|---|---|
| Groups of animals | Number of animals in a group | single ethanol injection | Repeated ethanol injection |
| Control (water) | 10 | $45.6 \pm 7.1$ | $93.0 \pm 15.5$ |
| 1st group claimed compositon | 10 | $8.2 \pm 2.7$ | $11.0 \pm 4.1$ |
| 2nd group (succinic acid) | 10 | $1.6 \pm 1.1$ | $24.9 \pm 3.8$ |
| Truth of the tests, p | | $<0.01$ | $<0.01$ |

The data of Table 4 show that after a single ethanol injection succinic acid has demonstrated higher alcoprotective detoxifying activity than the claimed composition, but the latter provides a longer effect thus being more advantageous than succinic acid at repeated ethanol injections.

The effect of the present composition on alcohol dependence of rats ("chronic alcoholics") was studied. The rats used in the experiment during a long time-period were given a free choice between 15% ethanol and water; said rats daily took 7–10 g of ethanol per 1 kg of animal weight. Two times a day for a period of two weeks the test group of animals was given (intrastomach) the present composition in the dosage of 3.75 mg/kg of animal weight, the control group of animals was given (intrastomach) a corresponding amount of water. Under the condition of free choice between 15% ethanol and water, daily ethanol consumption by individual rats was registered during 10 days before the administration of the present composition, during the first and second weeks within which said composition was administered, and during the first week after such administration. The data obtained are shown in Table 5. Said data show that the administration of the present composition does not cause increase in alcohol consumption

TABLE 5

The effect of the claimed composition on daily consumption of 15% ethanol by rats (ml, $M \pm m$)

| | | Stages | | | |
|---|---|---|---|---|---|
| Groups of animals | Number of animals per a group | 10 days before claimed composition | 1st week of claimed composition | 2nd week of claimed composition | 1st week after claimed composition |
| Control | 10 | $17.7 \pm 0.35$ | $18.0 \pm 0.12$ | $17.2 \pm 0.41$ | $18.2 \pm 0.20$ |
| Test | 10 | $16.9 \pm 0.48$ | $19.2 \pm 0.47$ | $18.0 \pm 0.42$ | $15.5 \pm 0.65$ |

The effect of the present composition on bioenergetic processes in animals liver has been studied. Liver homogenates of male mice were used in these studies. 60 min. before decapitation the test group consisting of 20 animals was given (intrastomach) the present composition in the dosage of 3.75 mg/kg of animal weight, the control group consisting of 20 animals was given (intrastomach) the corresponding amount of water. Breathing intensity of mice liver homogenates was determined by polarographic measurement of the volume of oxygen uptake using Clark electrode. The administration of the present composition to test animals resulted in significant increase in endogenic breathing rate (the breathing on endogenic substrates) which is manifested by a sharp increase in initial oxygen uptake by mice liver homogenates ($68.4 \pm 13.1$ nanog-atom of oxygen per mg of protein per sec. versus $32.6 \pm 10.7$ in the control, $p<0.07$).

Succinate-depending component of endogenic breathing was determined through studying breathing inhibition in homogenates of test and control animals at different concentrations of malonate (being a specific succinate dehydrogenase inhibitor) in incubating medium. The data obtained are shown in Table 6. Table 6 shows that in control animals only 35–40% of endogenic breathing of liver homogenates occurs due to the oxygenation of endogenic succinic acid, while in test animals succinate-depending component of endogenic breathing makes about 80% ($p<0.001$). During 55–65 min. after the decapitation of test animals the input of succinate-depending component into total endogenic breathing of liver homogenates increases.

Moreover the experiments have shown that when the present composition is administered, the endogenic breathing of mice liver homogenates (in contrast to the control animals and in contrast to the animals treated with succinic acid alone) is sensitive not only to malonate but also to amythal (a widely known NAD-depending substrates inhibitor).

A comparative study of the effect of the present composition and that of succinic acid on the activity of succinate dehydrogenase in stomach and liver tissues and in lymphocytes was carried out using female mice weighing 20–30 g each. The first group of animals was given the present composition (intrastomach) in the dosage of 4 mg/kg of animal weight, the second group was given (intrastomach) succinic acid in the same dosage, the control group was given (intrastomach) a corresponding amount of water. 40 min. later the animals were decapitated and succinate dehydrogenase activity was measured in cryostate sections of liver and stomach using histochemical analyses ("Arkhiv anatomii, gistologii i embriologii" 1969, No. 12, Medizina Publishers, Leningrad, pp.112–116), as well as in lymphocytes using cytochemical analyses ("Arkhiv anatomii, gistologii and embriologii", 1969, No. 5, Medizina Publishers, Leningrad, pp. 85–91).

TABLE 6

Inhibiting of endogenic breathing of mice liver homogenates by different malonate concentrations, (in %, $M \pm m$)

| Malonate conc. in incubating medium, M | 20 min. after decapitation | | | 55–65 min. after decapitation | | |
|---|---|---|---|---|---|---|
| | Control | Test | Truth of test, p | Control | Test | Truth of test, p |
| 1 | 2 | 3 | 4 | 5 | 6 | 7 |
| $5 \times 10^{-4}$ | $8.5 \pm 2.2$ | $27.2 \pm 2.9$ | $<0.05$ | $17.0 \pm 4.6$ | $37.0 \pm 5.8$ | $<0.05$ |
| $1 \times 10^{-3}$ | $9.6 \pm 3.7$ | $51.5 \pm 3.8$ | $<0.05$ | $20.0 \pm 5.1$ | $59.5 \pm 8.0$ | $<0.05$ |
| $1.5 \times 10^{-3}$ | $18.5 \pm 5.7$ | $65.7 \pm 3.1$ | $<0.05$ | $38.7 \pm 8.1$ | $67.5 \pm 8.7$ | $<0.05$ |
| $2 \times 10^{-3}$ | $36.2 \pm 10.3$ | $73.5 \pm 4.1$ | $<0.05$ | $46.6 \pm 3.3$ | $75.5 \pm 11.4$ | $<0.05$ |

The data obtained are shown in Table 7. These data show that the present composition activates succinate dehydrogenase in stomach mucosa, liver and lymphocytes and has an advantage over succinic acid.

This study has shown that the present composition stimulates bioenergetic processes in mitochondrions of different tissues. Its effect is realized through increases in endogenic substrates among tricarboxylic acids, in their oxydation rate as well as in succinate dehydrogenase activity.

TABLE 7

The effect of the present composition and that of succinic acid on the activity of succinate dehydrogenase in liver, stomach (in nanomoles of formazan of p-nitroviolet tetrazolium per minute per mg of protein, $M \pm m$) and that of lymphocytes (in granules of formazan of p-nitroviolet tetrazolium per hour per 50 cells, $M \pm m$) in mice.

| Groups of animals | Number of anim. per group | Tissue | | |
|---|---|---|---|---|
| | | Liver | Stomach | Lymphocytes |
| Control | 20 | $20.3 \pm 2.1$ | $14.3 \pm 1.7$ | $546 \pm 3.4$ |
| 1st group (claimed composit.) | 20 | $26.6 \pm 1.2$ | $30.8 \pm 1.0$ | $656 \pm 6.7$ |
| 2nd group (succinic acid) | 20 | $21.8 \pm 0.6$ | $26.3 \pm 3.0$ | $643. \pm 5.1$ |
| Truth of tests, p | | $<0.05$ | $<0.05$ | $<0.05$ |

Radioprotective effect of the present composition has been studied using male rats weighing 180–200 g each. The animals were subjected to gamma-irradiation in the dosage of 16 Gy using "Malva-2" plant (dosage rate: 1.4 Gy/min., field: 15×20, focal distance: 30 cm, voltage: 8 MeV, strength of current: 3.5 µA.)

The test group consisting of 10 animals 30 min. before the irradiation was given per os the present composition in the dosage of 2 mg/kg of animal weight, the control group consisting of 10 animals was given a corresponding amount (0.5 ml) of purified water. It has been found out that at the dosage of 16 Gy, which dosage is a lethal dosage for 100% of control animals, the administration of the present composition resulted in 33% survival, increase average life-time up to 9 days while in the control group it is 6.9 days.

Mortality curves at FIG. 1 show that maximum mortality values for the control rats coincide with the first mortality peak (FIG. 1, Curve 1), which is characteristic of high irradiation dosages while the protective effect of the present composition not only reduces mortality, but also shifts maximum values to the second mortality peak (FIG. 1, Curve 2).

In the course of the experiment a known radioprotector glutathione (GSH) was used as a comparative preparation (see "Studia Biophysica", 1975, No. 1, v. 53, Academy Press, Berling, E. Germany, DDR, pp. 121–124). This preparation was given i.p. to a group of 10 animals 30 min. before the irradiation in the dosage of 100 mg/kg of animal weight. With the dosage of 16 Gy and abovementioned irradiating conditions the administration of glutathione resulted in 100% mortality, while the life-time of rats was 10.2 days versus 6.9 days in the control group.

Glutathione causes a reduction in rat mortality in the first peak but to a lesser extent than the present composition, and causes an increase in mortality in the third peak (see FIG. 1, Curve 3) providing a much weaker radioprotective effect in comparison to the present composition.

According to the results thus obtained the present composition may be classified as a radioprotector of medium efficiency.

Special attention should be paid to the fact that the present composition is used in extremely low dosages (while an effective dosage of succinic acid for rodents is 2.7 g/kg of animal weight), which provides some correction of energy metabolism towards increasing radioresistance of an organism.

The effect of the present composition on acid-forming and secretory function of stomach mucosa has been studied using mice and dogs. In the course of the experiments dogs weighing 10–20 kg each having Belov stomach fistula, and mice weighing 20–30 g each were used.

The effect of the present composition in different dosages on acid-forming and secretory function was studied in dogs stomach glands. The present composition in 5 ml of water was introduced through stomach fistula before feeding the dogs and 30 min. later stomach secretion values were measured. The results are shown in Table 8.

TABLE 8

The effect of the present composition in different dosages on acid-forming and secretory function of dogs stomach mucosa (a group of 10 animals has been used)

| Dosages of claimed composition, mg/kg of anim. wt. | Acid-forming function of stomach, M ± m Gastric juice pH | Secretary function of stomach, M ± m | |
|---|---|---|---|
| | | Gastric juice secretion, ml/hour | Pepsin secretion, mg/hour |
| 0 (before feeding) | 7.3 ± 0.4 | 7.0 ± 1.0 | 0.48 ± 0.06 |
| 0.36 | 5.6 ± 0.6 | 15.6 ± 1.3 | 1.28 ± 0.07 |
| Truth of tests, p | <0.02 | <0.001 | <0.01 |
| 3.6 | 4.7 ± 1.1 | 20.9 ± 4.1 | 2.28 ± 0.08 |
| Truth of tests, p | <0.05 | <0.01 | <0.001 |
| 5.4 | 4.75 ± 1.5 | 21.2 ± 3.1 | 2.31 ± 0.07 |
| Truth of tests, p | — | — | — |

Note: p is given in comparison with the values for preceding dosage.

As shown in Table 8 the dosage of 3.6 mg/kg of animal weight is the optimal dosage for stimulating functional activity of stomach glands. Besides it has been found that the effect of 0.1 optimal dosage of the present composition ceases in 30–40 min. after the introduction, while in 80 min. after the introduction of an optimal dosage the amount of gastric juice and the levels of HCl and pepsin remain higher than the same levels before feeding. It should be noted that the introduction of 0.1 optimal dosage of the present composition to dogs through stomach fistula followed by subsequent introduction of optimal dosage (40 min. later, when secretion abates) does not reduce the stimulating effect of the present composition, but on the contrary potentiates said effect, significantly increasing stomach glands activity over a prolonged period.

The effect of the present composition on acid-forming and secretory function of stomach glands as well as on succinate dehydrogenase activity in stomach mucosa and lymphocytes in peripheral blood in dogs has been studied. The present composition was introduced in 5 ml of water in the dosage of 3.5 mg/kg of animal weight through stomach fistula to dogs on an empty stomach, and 40 min. later the values characterizing stomach secretion and succinate dehydrogenase activity have been taken. The data obtained are shown in Table 9. These data demonstrate that the present composition increases significantly both the functional activity of stomach glands and the activity of succinate dehydrogenase of stomach mucosa. Therefore the present composition produces an effect on stomach functioning by inducing bioenergetic processes, specifically succinate-depending oxydation in mitochondria of different tissues.

A comparative study of the effect of the present composition in the dosage of 3.6 mg/kg of animal weight and that of succinic acid in the same dosage on stomach mucosa functioning and on succinate dehydrogenase activity in dogs (a group of 10 animals) has been carried out. The study has demonstrated that the stimulation of stomach glands and fermentative activity with succinic acid has given less expressed results and in contrast to the present composition the effect of said acid on stomach secretion has been abated 20 min. after its introduction.

The effect of the present composition and that of succinic acid on acid-forming and secretory functions of stomach mucosa and on the number of macromolecules contained in stomach and liver tissues in mice has been studied. The first group of animals was given (intrastomach) on an empty stomach the present composition in the dosage of 3.5 mg/kg of animal weight in 0.2 ml, the second group of animals was given in the same manner succinic acid in the same dosage, the control group of animals was given a corresponding amount of water. 35–45 min. later the mice were decapitated, and stomachs and livers were extracted. Stomachs were washed with water through cardiac opening and the washing from the antral opening were collected. Stomach contents (5 ml of washings) were used to determine pH, pepsin and total protein content. Stomach was refilled with water, frozen in cryostate and serial section having the thickness of 6–8 microns were made beginning from low curvature and parallel to stomach longer axis. In the sections of stomach bottom and body having a total weight of 50–90 mg, protein and nucleic acids content was determined. The results of this study are shown in Tables 10 and 11.

TABLE 9

The effect of the present composition on acid-forming and secretory activity of stomach mucosa and on the activity of succinate dehydrogenase of stomach mucosa as well as that of peripheral lymphocytes in dogs (a group of 15 animals)

| | Acid-forming activity | Secretory activity | | Succinate dehydrogenase activity | | Lymphocytes granules of formazan of |
| | | | | M ± m Stomach mucosa, nanomoles of formazan of | | |
| | M ± m Gastric | Protein secretion | Pepsin secretion, | p-nitroviolet tetrazolium per min/mg | | p-nitroviolet tetrazolium/ |
| Stages 1 | juice pH 2 | mg/hour 3 | mg/hour 4 | tissue 5 | protein 6 | hour/50 cells 7 |
|---|---|---|---|---|---|---|
| Empty st. | 6.0 ± 0.6 | 151.8 ± 39.0 | 1.55 ± 0.4 | 22.1 ± 2.7 | 21.3 ± 3.1 | 796.7 ± 46.4 |
| Present composit. | 3.9 ± 8.5 | 311.6 ± 77.0 | 2.82 ± 0.6 | 29.9 ± 2.6 | 23.9 ± 1.7 | 899.2 ± 44.3 |
| Truth of tests | <0.01 | <0.05 | <0.001 | <0.02 | <0.05 | <0.01 |

TABLE 10

The effect of the present composition and that of succinic acid on acid-forming and secretory activity of stomach mucosa in mice

| | | Acid-forming activity M ± m pH of stomach contents | Secretory activity, M ± m | |
| | | | Total protein amount in stomach contents, mg | Pepsin amount in stomach contents, µg |
| Groups 1 | Number of animals 2 | 3 | 4 | 5 |
|---|---|---|---|---|
| Control | 25 | 5.6 ± 0.2 | 2.6 ± 0.4 | 14.4 ± 1.2 |
| 1st group (present composition | 20 | 5.0 ± 0.3 | 4.8 ± 0.6 | 23.3 ± 2.0 |
| 2nd group (succinic acid) | 11 | 5.7 ± 0.2 | 3.9 ± 0.9 | 18.7 ± 2.1 |
| Truth of tests, p | | — | <0.01 | <0.01 |

Tables 10 and 11 show that the present composition has an advantage over succinic acid in stimulating functional activity of stomach glands and in synthesizing macromolecules in liver and stomach tissues in mice. Thus the stimulation of stomach secretion and fermentative activity of succinate dehydrogenase induced by the present composition in stomach and liver tissues (see Table 7) is the result of activation of nucleic processes in said tissues.

Cholera preventing effect of the present composition has been studied in vitro and in vivo using Mechnikov vibrio.

TABLE 11

The effect of the present composition and that of succinic acid on macromolecules content in stomach and liver tissues in mice (M ± m, in 100 mg of tissue).

| | Number of animals in a group | Stomach | | | Liver | | |
| Groups of animals | | Protein mg | RNA µg | DNA µg | Protein mg | RNA µg | DNA µg |
|---|---|---|---|---|---|---|---|
| Control | 25 | 12.7 ± 0.7 | 60.0 ± 3.5 | 14.8 ± 1.6 | 14.7 ± 0.7 | 73.1 ± 3.0 | 15.4 ± 1.4 |
| 1st group (present composition) | 20 | 16.5 ± 0.3* | 67.6 ± 3.1* | 20.5 ± 2.7* | 16.6 ± 0.9* | 72.2 ± 3.1 | 20.9 ± 2.2* |
| 2nd group (succinic acid) | 11 | 12.1 ± 0.9 | 70.0 ± 4.7* | 13.1 ±1.1 | 14.4 ± 1.2 | 74.5 ± 4.4 | 15.6 ± 2.7 |

Note: *means that the difference from the control is true, $p < 0.05$.

0.1 ml of vibrio culture in titer $10^8$ was introduced into 1 ml of dissolved present composition at different concentrations of active ingredient (see Table 12) and incubated at 37° C. for 1 hour. Then a sample of each incubated medium was cultured in bottles containing alkaline peptone broth at 37° C. To provide vibrio indentification every 24 hours a sample of the contents of each bottle was cultured in alkaline nutrient agar at 37° C. Every 48 hours the number of vibrio colonies on agar was counted. The results are shown in Table 12. The Table shows that the present composition is given concentrations (being nearly the same as such concentrations in stomach after oral administration of the present composition) inhibits vibrio growth and development.

For the experiments mice weighing 20–25 g each were used. The test group consisting of 20 animals was orally administered 3 times a day a solution of the present composition in the dosage of 3.75 mg/kg of animal weight, to the control group consisting of 20 animals water was administered in the same amount. On the 2nd day the control group was given 0.3 ml of vibrio culture suspension in titer $10^8$. The test group was treated in the same manner, but 20 min. before introducing vibrio the test group received a solution of the present composition in the above dosage.

TABLE 12

The effect of the present composition in different concentrations on Mechnikov vibrio viability

| Present composition ingredients | Concentrations of the present composition, μM | | | |
|---|---|---|---|---|
| Succinic acid | 3 | 0.3 | 0.03 | 0.003 |
| Citric acid | 0.5 | 0.05 | 0.005 | 0.0005 |
| Number of vibrio colonies | 0 | 0 | 0 | 0 |

In an hour after introducing vibrio culture the animals were decapitated, stomachs were extracted and samples of stomachs contents were incubated in bottles containing alkaline peptone broth at 37° C. To provide vibrio identification every 24 hours a sample of the contents of each bottle was cultured in alkaline nutrient agar at 37° C. In 48 hours the number of vibrio colonies on agar was counted.

As a result of this study vibrio has been found in stomachs of control animals, while in test animals no growth of vibrio colonies has been observed.

Acute toxicity of the present composition has been studied using while mice weighing 20–25 g each and white rats weighing 200–250 g each (groups consisting of 30 animals). It has been found that with per os administration, $LD_{50}$ of the present composition for mice is 5000 mg/kg of animal weight, and for rats it is 4880 mg/kg of animal weight; with i.p. administration $LD_{50}$ for mice is over 2400 mg/kg of animal weight.

Chronic toxicity of the present composition has been studied by administering said composition to dogs weighing 3–7 kg each (a group of 8 animals) and to white rats weighing 180–200 g each (a group of 40 animals) in the dosages of 3, 7, 37 and 300 mg per kg of animal weight (per os administration) during 6 months. The study has shown that with chronic administration the present composition does not cause pathological changes in peripheral blood, urine composition, marrow morphology, and brain. Moreover the present composition does not produce teratogenic and mutagenic effects, it does not affect coagulation, immune system, reproductive function and hypophysis-adrenal system.

Clinical trials of the present composition have been carried out in narcological hospitals using 320 alcoholic patients and 20 healthy volunteers.

The effect of the present composition on the process of acute alcohol intoxication in 10 healthy people has been studied. The effect of the present composition was evaluated using expert assessments and evaluating temporal speech characteristics. Before the trials the volunteers have been subjected to routine examination including the process of sleeping, fatiguability, functioning of cardio-vascular system; the data of the latest alcohol drinking has been asked for. The present composition in the dosage of 3.75 mg/kg of body weight and placebo were administered to the volunteers (in gelatin capsules) 20 min. before taking 40% alcohol solution in the dosage of 0.8 g/kg of body weight. Each volunteer was observed in the state of alcohol intoxication after having received placebo and after having received the present composition. After drinking alcohol the volunteers have been continuously observed to study the dynamics of intoxication and its characteristic features. In 75% of cases experts have noticed a clearly expressed effect of the present composition in comparison with placebo. The effect of the present composition was better observed in patients with disinhibited psychomotor reactions. With the present composition no speed and motor excitation has been observed, self-control over behavior and talking is better, languor, psychic inhibition, disarthria disappear. In general the effect of the present composition on a volunteer in comparison with placebo has manifested itself in smoother behavioral reactions. In 50% of cases abatement of intoxication required less time in comparison with placebo, alcohol intoxication caused less or even no after-effects, such as headache, nausea, weakness, worsened appetite. Moreover the volunteers had the feeling that with the present composition alcohol intoxication was "unusual", they could preserve self-control over motions and talking.

Figure 2A:
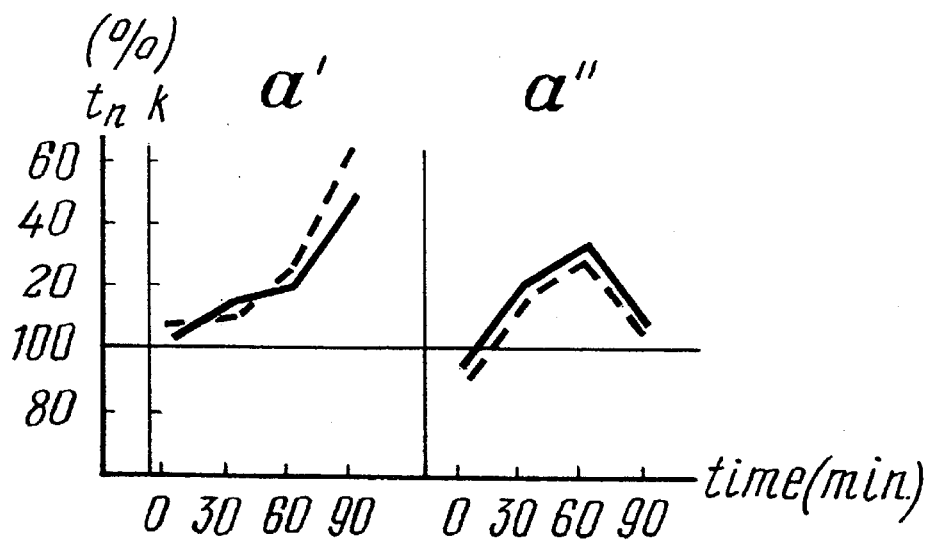
FIG. 2A shows the effect of the present composition with respect to the temporal characteristics of speech of the tested patients from the 1st test group.
Figure 2B:
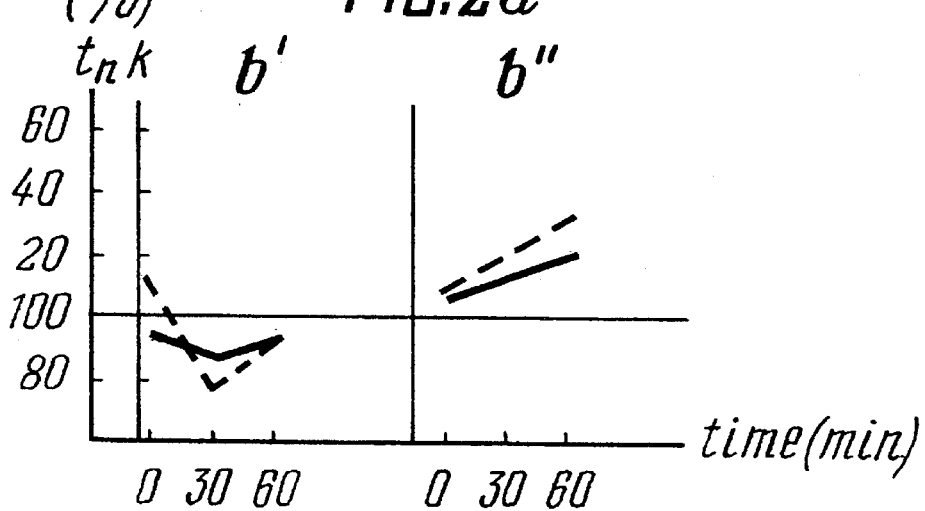
FIG. 2B shows the effect of the present composition with respect to the temporal characteristics of speech of the tested patients from the 2nd test group.
Figure 2C:
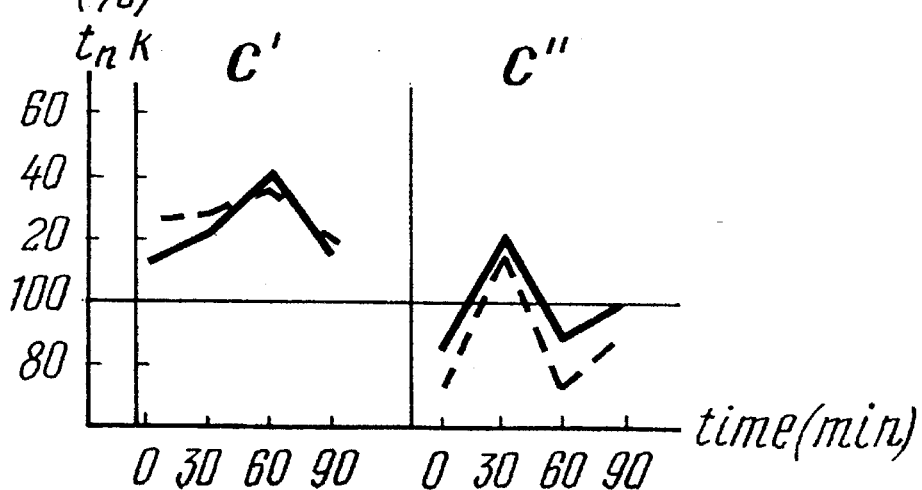
FIG. 2C shows the effect of the present composition with respect to the temporal characteristics of speech of the tested patients from the 3d test group.

Antialcoholic activity of the present composition in the same patients has been studied by evaluation of temporal speech characteristics. Based on the results of speech characteristics the volunteers have been divided into 3 groups. The results of this study are shown at FIGS. 2A, 2B and 2C, wherein $t_n$ is a total pauses duration in percent to the background value; k is a relative pauses duration in percent to the background value; 100% is the background value, i.e. arithmetic mean of individual speech characteristics of volunteers (in peace) during 3 days training; full line shows variations in total pauses duration, and dotted line shows variations in relative pauses duration during the experiment (p<0.05).

To provide better understanding each figure is subdivided into two, wherein 2A', 2B' and 2C' show speech parameters variations after drinking alcohol with placebo, and 2A", 2B" and 2C" show speech parameters variations after drinking alcohol with the present composition, respectively. The both speech patterns for the volunteers of the 1st group after drinking alcohol with placebo developed in the same direction, that is, showed a tendency to slowing down: in 90 min. after drinking total pauses duration increased by 53%, and relative pauses duration increased by 68% in comparison with the background value (see FIG. 2A, Part 2A'). After drinking alcohol with the present composition variations of these parameters on the 60th minute were 31 and 28% of the background value, respectively, and in 90 min, these parameters reduced to the initial values (see FIG. 2A, Part 2A').

The volunteers of the 2nd group after drinking alcohol with placebo and with the present composition showed insignificant variations of speech parameters in combination to the background values, but these variations developed in different directions. (see FIG. 2B, Parts 2B' and 2B"). The volunteers of the 3d group showed the same tendency: speech parameters developed in different directions. In spite of the difference in initial values parameters dynamics on the 60th minute demonstrates expressed acceleration (FIG. 2C, Part 2C') or slowing down (FIG. 2C, Part 2C") of speech.

It should be noted that the speech of the volunteers of the 1st and 3d groups after drinking alcohol with the present composition became normal very soon. Therefore the present composition has a clear alcoprotective and detoxifying activity.

The effect of the present composition on alcohol content in breathing air has been studied (in terms of alcohol content in blood) using 10 healthy volunteers. The volunteers were given water solution of the present composition in the dosage of 3.75 mg/kg of body weight 20 min. before drinking 40 % ethanol in the dosage of 0.5 g/kg of body weight. Alcohol content in breathing air has been determined at set intervals after drinking. The study has demonstrated that the antitoxic activity of the present composition results from accelerated alcohol removal from an organism and from an increase in alcohol elimination constant from 0.1–0.25 to 0.6–0.8 ghour$^{-1}$ ($p<0.05$).

The effect of the present composition on the development of alcohol abstinence syndrome has been studied in patients suffering alcoholism of 2nd–3d stages, who came to the clinic to stop fits of hard drinking. All patients came to the clinic suffering alcohol intoxication with ethanol content in blood being 1.5–3.5 g/kg of body weight. The 1st group was subjected to routine therapy including administration of neuroleptics, tranquilizers and antidepressants. The 2nd group was subjected to routine therapy and was administered the present composition in the dosage of 3–4 mg/kg of body weight per taking (total daily dose being 9–20 mg/kg of body weight). The 3d group received only the claimed composition in the abovementioned dosages.

Patients conditions were assessed in balls characterizing the degree to which main alcohol abstinence simptoms were manifested. Each symptom was assessed by a 4 balls system (from 0 to 3 balls). The data obtained are shown in Table 13. Table 13 shows that the present composition with respect to its alcohol detoxifying activity is no less effective than a powerful routine therapy, though the latter produces a number of undesirable side-effects. (such as encephalopathy, tremor, etc.)

TABLE 13

The effect of the present composition on the condition of patients suffering alcohol abstinence syndrome (in balls, M ± m).

| Groups of patients | Number of patients in a group | Stages | | |
|---|---|---|---|---|
| | | Before administration | 2 days of taking preparations | 3 days of taking preparations |
| 1st group (routine therapy) | 25 | 12.2 ± 0.91 | 6.4 ± 0.95 | 2.1 ± 0.23 |
| 2nd group (routine therapy + present composition | 27 | 13.5 ± 1.2 | 5.6 ± 0.65 | 2.3 ± 0.55 |
| 3d group (Present composition | 11 | 14.4 ± 2.4 | 5.6 ± 1.00 | 1.7 ± 0.70 |

It has been found that 15–20 min. after taking the present composition the patients suffering alcohol intoxication show lessened excitation, they regain self-appraisal, tell that their "minds were clearing", and on the 1st day of administration of the present composition improved patients condition and appetite have been observed.

The assessment of the rate of counting (addition of pairs of simple numbers, totally 184 pairs) showed that in 10–18 hours after having arrived into the clinic all patients from the 3d group (receiving the present composition) were able to go through the task and the rate of counting was 32±1.2 signs per minute. In the 1st group of patients subjected to routine therapy this rate was 19±1.8 signs per minute ($p<0.001$), and 25% of patients failed to go through the task due to highly inhibited reactions. Among said groups the difference in time required to go through the task, could be observed even after 3 days in clinic.

The effect of the present composition on patients suffering alcoholism of 2nd–3d stages and being subjected to ambulatory treatment has been studied. The 1st group of patients was examined during the period of daily alcohol drinking in the dosage of 1–1.5 g/kg of body weight, and the 2nd group was examined during fits of hard drinking. The present composition was administered to the patients in the dosage of 3–4 mg/kg of body weight 3–4 times a day during 3–4 days of alcohol drinking and 3–4 days after alcohol drinking. In patients of the 1st group the present composition changed the pattern of alcohol intoxication: euphoria stage developed without clear disinhibition, self-control was improved, aggressive behavior was reduced significantly. Appetite improved, postintoxication disorders were reduced significantly. All this resulted in less alcohol drinking (up to abstination), improved general condition of patients. It has been noted that when the present composition was administered during remission period, then one-time alcohol drinking which later caused recidivation, had no after-effects (no abstinence syndrome) and did not cause recidivation. The patients of the 2nd group felt the effect of the present composition as soon as 1–2 hours after taking it: their "mind cleared", they "became sober". 75% of the patients felt less or no alcohol dependence, they told to their doctors that they "don't want to drink any more". Such feeling appeared in different periods, usually from 4 to 12 hours after taking the present composition, but it took 1–2 days to discontinue a fit of hard drinking. The administration of the present composition caused positive changes in symptoms of postintoxication. The patients felt better, their appetites improved, they felt "less languid, jaded", their minds cleared. 15% of patients while receiving the present composition continued to drink alcohol during 2–3 days, but the daily doses of alcohol were reduced significantly.

The effect of the present composition on drunk patients receiving ambulatory treatment to discontinue alcohol abstinence syndrome has been studied. The 1st group of patients was subjected to routine therapy including the administration of tranquilizers, antidepressants, sodium oxobutirate. The 2nd group of patients was administered the present composition in solution in the dosage of 3–4 mg/kg of body weight per taking (total daily dosage of 9–20 mg/kg of body weight). Patients conditions were assessed in balls characterizing the degree to which main alcohol abstinence symptoms were manifested. The obtained data are shown in Table 14.

TABLE 14

The effect of the present composition on the conditions of patients receiving treatment to discontinue alcohol abstinence syndrome (in balls, M ± m)

| Groups of patients | Number of patients in a group | Stages | |
|---|---|---|---|
| | | 1st day of taking the preparations | 2nd day of taking the preparations |
| 1st group (routine therapy) | 10 | 9.9 ± 1.1 | 4.2 ± 1.2 |
| 2nd group (present composition) | 19 | 2.1 ± 0.09 | 0.8 ± 0.03 |
| Truth of the tests | | <0.01 | <0.01 |

Table 14 shows that in the 2nd group of patients practically no abstinence symptoms were observed even 12–18 hours after taking the present composition. 50% of patients on the 1st day of treatment noted lessened "thirst for alcohol", cheerfulness, improved appetite.

The effects of the present composition on the patients being in asthenic stage of alcohol abstinence syndrome after lessening of acute stage have been studied. The patients came to clinic in order to discontinue fits of hard drinking or received ambulatory treatment. The present composition was administered beginning from the 3d day after drinking alcohol; it was administered in the dosage of 3–4 mg/kg of body weight (in solution) 2–3 times a day during 4–6 days. 80–90% of patients treated with the present composition noted that they began to feel much better, their sleep and appetite normalized, symptoms of dyspepsia and stomach pains disappeared. In hypertensive patients normalization of blood pressure was observed.

Thus the results of these studies have shown that the present composition has alcoprotective and alcohol detoxifying activities, accelerates alcohol removal from an organism, reduces alcohol drinking and alcohol dependence.

To study the stimulating effect of the present composition on energy metabolism, clinical trials have been carried out using 20 hypotensive patients. Systolic and diastolic pressures were measured in the patients before oral administration of the present composition in the dosage of 3.75 mg/kg of body weight and 20 min. after such administration. The data obtained are shown in Table 15.

TABLE 15

The effect of the present composition on blood pressure in hypotensive patients.

| Stages | Blood pressure, mm Hg, M ± m | |
|---|---|---|
| | Systolic pressure | Diastolic pressure |
| Before the present composition | 95 ± 2.9 | 62 ± 2.3 |
| After the present composition | 122 ± 3.3 | 78 ± 3.0 |
| Truth of the tests, p | <0.05 | <0.05 |

Table 15 shows that the present composition improves energy metabolism, which is manifested in increased tonus of smooth cardiac musculature.

The stimulating effect of the present composition on acid-forming and secretory function of stomach mucosa have been studied using 11 healthy volunteers and 498 patients suffering different forms of gastroenteropathology: chronic surface gastritis with retained secretion (97 patients), chronic surface gastritis with reduced secretion (74 patients), chronic wide-spread atrophic gastritis with reduced secretion (177 patients), chronic gastritis with increased secretion accompanying stomach ulcer (21 patients), chronic gastritis with increased secretion accompanying duodenum ulcer (84 patients), diffused gastritis with affected fundic and antral sections (30 patients) and chronic hypertrophic gastritis (15 patients).

The diagnoses were verified on the basis of all presently used methods for diagnosing gastroenterological diseases. The present composition was administered orally in solution in 15 ml of water in the dosage of 4 mg/kg of body weight. Pentagastrin in the dosage of 6 µg/kg of body weight and histamine in the dosage of 0.1 ml of 0.1% solution were used as comparative preparations. Gastric juice was extracted using continuous pulse vacuum aspiration with negative pressure of 50–60 mm Hg on an empty stomach; the extraction was carried out 20 min. after taking the present composition or comparative preparations. Additionally intrastomach pH-metry was carried out (on an empty stomach and after taking the present composition or comparative preparations) using acidograph with aspiratory pH probe. Before introducing the present composition and comparative preparations and after that pH levels were registered and "alkaline time" was determined using Noller test. Having deciphered pH-gramms, pH levels, "alkaline time" (AT), hydrogen ions secretion rate (HISR), kinetic function of acid formation (KFA) were determined.

The effect of the present composition on stomach secretion in patients suffering chronic gastritis has been studied. The results of this study are shown in Table 16. Table 16 shows that the present composition produces a stimulating effect on all characteristics of stomach secretion causing increase in secretion amount, acidity, specific weight of acid component, fermentation, acid and pepsin debit; pH levels in stomach fall to acid values, KFA increases, AT is reduced, HISR accelerates.

A comparative study of the stimulating effect of pentagastrin and that of the present composition in patients suffering chronic gastritic has been carried out. It has found that the both preparations produce nearly the same effect on stomach secretion (with respect to gastric juice amount, acidity, partial acid secretion, pepsin content, acid and pepsin debit) in the same patients ($p<0.5$). At the same time 12 of 50 patients suffering chronic gastritis were refractory to pentagastrin, i.e. after taking this preparation acidity, pepsin content, hydrochloric acid debit and pepsin debit remained at zero levels. With intragastric pH-metry initial levels of pH in these patients varied from 3.5 to 6.8, and after Noller test these levels increased to alkaline values (8–9) which levels remained the same during the test period (1–1.5 hours). After pentagastrin stimulation of stomach secretion pH levels in the same patients changed insignificantly (from 6.51±1.06 to 4.69±0.92; $p<0.25$), and Noller test did not cause AT reduction ($p<0.5$).

TABLE 16

The effect of the present composition on stomach secretion in patients suffering chronic gastritis (a group of 50 patients)

| Stomach secretion characteristics | Basal secretion | Stimulated secretion | Truth of the test, p |
|---|---|---|---|
| Stomach contents volume, liter per hour, M ± m | 0.07 ± 0.005 | 0.11 ± 0.01 | <0.002 |
| Acidity, mmol per liter, M ± m | 5.32 ± 1.37 | 49.60 ± 5.83 | <0.001 |
| Acid secretion percent, M ± m | 19.62 ± 0.95 | 38.84 ± 2.12 | <0.001 |
| Hydrochloric acid debit, mmol per hour M ± m | 0.28 ± 0.08 | 4.04 ± 0.56 | <0.001 |
| Pepsin content, mg per ml, M ± m | 0.55 ± 0.02 | 0.25 ± 0.03 | <0.001 |
| Pepsin debit, mg per hour, M ± m | 3.22 ± 1.28 | 19.85 ± 3.67 | <0.001 |
| pH, M ± m | 8.01 ± 0.18 | 2.04 ± 0.38 | <0.001 |
| KFA, mg %, M ± m | 2.07 ± 0.37 | 9.93 ± 0.77 | <0.001 |
| AT, min., M ± m | 20.90 ± 2.52 | 12.36 ± 2.10 | <0.02 |
| HISR, pH units per min., M ± m | 1.72 ± 0.36 | 3.73 ± 0.52 | <0.02 |

The effect of the present composition on stomach secretion in patients of this group has been studied. The results of this study are shown in Table 17. Table 17 shows that the present composition, in contrast to pentagastrin, stimulates acids and frements formation, but the values of stomach contents volume differ insignificantly after the stimulations with the present composition and pentagastrin. This effect of the present composition is related to the fact that the composition activates bioenergetic and metabolitic processes in stomach mucosa and lessens or eliminates functional inhibition of delomorphous and central cells of stomach glands; therefore this composition may be used for the treatment of patients suffering chronic gastritis with pentagastrinrefractive achlorhydria.

TABLE 17

The effect of the present composition on stomach secretion in patients suffering chronic gastritis with pentagastrinrefractive achlorhydria (a group of 12 patients).

| Stomach secretion characteristics | Pentagstrin stimulated secretion | Present composition stimulated secretion | Truth of tests, p |
|---|---|---|---|
| Stomach contents volume, liter per hour, M ± m | 0.067 ± 0.15 | 0.111 ± 0.26 | >0.25 |
| Acidity, mmol per liter, M ± m | 0 ± 0 | 32.0 ± 3.44 | <0.001 |
| Acid secretion, % M ± m | 15.25 ± 0.86 | 25.25 ± 1.93 | <0.001 |
| Hydrochloric acid debit, mmol per hour, M ± m | 0 ± 0 | 1.05 ± 0.19 | <0.001 |
| Pepsin content, mg per ml, M ± m | 0 ± 0 | 0.065 ± 0.02 | <0.01 |
| Pepsin debit, mg per hour, M ± m | 0 ± 0 | 1.21 ± 0.34 | <0.002 |

Clinical trials showed that the effect of the present composition and that of pentagastrin depended insignificantly on the character of pathology; these effects depended mainly on the succession in which these preparations were administered. Thus, the both preparations produced nearly the same effect on stomach secretion in patients suffering chronic gastritis accompanying stomach and duodenum ulcers (p<0.5). But when pentagastrin was administered in a day after the administration of the present composition it produced a much stronger effect on stomach secretion in patients of this group (see Table 18).

TABLE 18

The effect of pentagastrin (when administered after the present composition) on stomach secretion in patients suffering chronic gastritis accompanied by stomach and duodenum, ulcers (a group of 24 patients).

| Stomach secretion characteristics | Basal secretion | Stimulated with present composition secretion | Pentagastrin stimulated secretion | Truth of tests, p |
|---|---|---|---|---|
| Secretion volume, ml, M ± m | 56 ± 4.2 | 120 ± 6.3 | 178 ± 12.7 | <0.05 |
| pH, M ± m | 3.5 ± 0.29 | 1.7 ± 0.11 | 1.4 ± 0.14 | <0.05 |
| Hydrochloric acid debit mmol/h, M ± m | 2.0 ± 0.27 | 9.2 ± 0.68 | 17 ± 1.44 | <0.05 |
| Pepsin debit, mg/h, M ± m | 4.5 ± 0.6 | 5.9 ± 0.75 | 5.0 ± 1.05 | — |

At the same time when the present composition wad administered in a week after pentagastrin, the effects of said preparations were nearly identical (p<0.5). Thus, the present composition even after one taking causes the stimulation of bioenergetic processed and physiological activity of stomach mucosa which remains at least during 24 hours.

The study was carried out on the effect of the present composition on acid-forming function of stomach mucosa in patients suffering different forms of chronic gastritis (see Table 19); in healthy volunteers (using fractional study of stomach contents) (see Table 20); in patients suffering surface chronic gastritis with retained secretion and chronic atrophic gastritis with reduced secretion (see Table 21); in patients suffering chronic gastritis accompanying stomach and duodenum ulcer (see Table 22).

Tables 19, 20, 21, and 22 show that the present composition produces a clearly expressed stimulating effect on stomach mucosa both in healthy volunteers and in patients suffering different forms of gastritis.

TABLE 19

The effect of the present composition on acid-forming function of stomach mucosa in patients suffering different forms of chronic gastritis

| Chronic gastritis form 1 | Total acidity meq./liter, M ± m | | | | | |
|---|---|---|---|---|---|---|
| | Basal 2 | Stimulated 3 | Truth of tests p 4 | Basal 5 | Stimulated 6 | Truth of tests p 7 |
| 1. Chronic surface gastritis (retain. secretion) (97 patients) | 3.51 ± 2.32 | 15.56 ± 3.62 | <0.05 | 1.13 ± 0.90 | 7.34 ± 1.23 | <0.05 |
| 2. Chronic surface gastritis (reduced secretion) (74 patients) | 1.04 ± 0.34 | 5.70 ± 0.52 | <0.05 | 0.12 ± 0.06 | 2.40 ± 0.32 | <0.05 |
| 3. Chronic wide-spreed gastritis (atrophic, reduced secretion) (177 patients) | 0.47 ± 0.09 | 2.92 ± 0.34 | <0.05 | 0.00 ± 0.00 | 0.32 ± 0.03 | <0.05 |
| 4 Chronic gastritis/reduced secretion/stomach ulcer (21 patients) | 3.05 ± 0.35 | 10.18 ± 1.56 | <0.05 | 0.55 ± 0.05 | 1.59 ± 0.09 | <0.05 |
| 5. Chronic gastritis/reduced secretion/ duodenum ulcer (84 patients) | 8.6 ± 4.52 | 17.50 ± 6.53 | >0.05 | 4.04 ± 2.21 | 7.04 ± 2.56 | >0.05 |

TABLE 20

The effect of the present composition on acid-forming function of stomach mucosa in healthy volunteers (a group of 11 volunteers)

| Gastric juice portion number | Free hydrochloric acid, meq./liter, M ± m | Total hydrochloric acid, meq./liter, M ± m |
|---|---|---|
| 1st portion (0 min. basal secretion) | 6.6 ± 3.4 | 23.3 ± 16.3 |
| 2nd portion (in 15 min.) | 7.0 ± 2.3 | 25.3 ± 9.0 |
| 3d portion (in 30 min.) | 11.3 ± 4.0 | 25.6 ± 13.3 |
| 4th portion (in 45 min.) | 11.3 ± 4.0 | 27.6 ± 13.3 |
| 5th portion (in 60 min) | 5.6 ± 2.3 | 18.6 ± 5.3 |
| | Stimulation with the present composition | |
| 6th portion (in 75 min., stimulated secretion) | 22.3 ± 7.0 | 89.3 ± 7.0 |
| 7th portion (in 90 min.) | 55.0 ± 24.3 | 81.3 ± 23.3 |
| 8th portion (in 105 min.) | 44.0 ± 6.6 | 72.3 ± 17.6 |
| 9th portion (in 120 min.) | 47.3 ± 11.0 | 64.6 ± 26.0 |

TABLE 21

The effect of the present composition on acid-forming function of stomach mucosa in patients suffering chronic gastritis taking into account the clinico-morphological version of the disease

| Gastric juice portion No. 1 | Chronic surface gastritis with retained secretion (a group of 97 patients) | | Chronic atrophic gastritis with reduced section (a group of 48 patients) | |
|---|---|---|---|---|
| | Free hydrochloric acid meq./Liter M ± m 2 | Total hydrochloric acid meq./liter M ± m 3 | Free hydrochloric acid meq./liter M± 4 | Total hydrochloric acid meq./liter M ± m 5 |
| 1st portion (0 min., basal secretion) | 2.5 ± 0.5 | 21.5 ± 7.7 | 0 ± 0 | 8.4 ± 1.2 |
| 2nd portion (in 15 min.) | 4.5 ± 1.5 | 26.7 ± 7.0 | 0 ± 0 | 15.5 ± 5.16 |
| 3d portion (in 30 min.) | 7.0 ± 2.5 | 28.0 ± 6.6 | 0 ± 0 | 15.6 ± 5.8 |
| 4th portion (in 45 min.) | 11.5 ± 2.6 | 33.0 ± 6.0 | 0 ± 0 | 14.0 ± 5.6 |
| 5th portion (in 60 min.) | 15.0 ± 3.0 | 39.0 ± 4.0 | 0 ± 0 | 12.8 ± 6.5 |
| | Stimulation with the present composition | | | |
| 6th portion (in 75 min., stimulated secretion) | 16.5 ± 10.0 | 51.7 ± 21.6 | 1.6 ± 1.2 | 24.0 ± 7.68 |
| 7th portion (in 90 min.) | 27.5 ± 8.6 | 56.0 ± 23.0 | 0 ± 0 | 10.0 ± 1.2 |
| 8th portion (in 105 min.) | 29.0 ± 8.3 | 54.5 ± 23.3 | 0 ± 0 | 10.8 ± 1.76 |
| 9th portion (in 120 min.) | 30.5 ± 12.6 | 54.5 ± 19.8 | 0 ± 0 | 8.8 ± 1.36 |

TABLE 22

The effect of the present composition on acid-forming function of stomach mucosa in patients suffering chronic gastritis accompanying stomach and duodenum ulcers

| Gastric juice portions No. 1 | Chronic gastritis/ stomac ulcer (a group of 21 patients) | | Chronic gastritis/ duodenum ulcer (a group of 84 patients | |
|---|---|---|---|---|
| | Free hydrochloric acid, titration units, M ± m 2 | Total hydrochloric acid, titration units, M ± m 3 | Free hydrochloric acid, titration units, M ± m 4 | Total hydrochloric acid, titration units, M ± m 5 |
| 1st portion (0 min., basal secretion | 0 ± 0 | 15.0 ± 8.5 | 16.0 ± 3.1 | 52.0 ± 9.2 |
| 2nd portion (in 15 min) | 0 ± 0 | 27.0 ± 6.0 | 50.0 ± 15.4 | 46.0 ± 23.7 |
| 3d portion (in 30 min.) | 0 ± 0 | 20.0 ± 6.2 | 59.0 ± 16.5 | 127.0 ± 20.5 |
| 4th portion (in 45 min.) | 0 ± 0 | 28.0 ± 8.5 | 86.0 ± 14.3 | 100.0 ± 19.8 |
| 5th portion (in 60 min.) | 0 ± 0 | 27.0 ± 12.2 | 42.0 ± 21.6 | 68.0 ± 23.3 |
| Stimulation with the present composition | | | | |
| 6th portion (in 75 min.) | 23.0 ± 8.7 | 59.0 ± 11.5 | 80.0 ± 13.2 | 93.0 ± 20.8 |
| 7th portion (in 90 min.) | 57.0 ± 10.2 | 81.0 ± 12.5 | 76.0 ± 17.4 | 88.0 ± 25.8 |
| 8th portion (in 105 min.) | 58.0 ± 8.5 | 97.0 ± 17.5 | 50.0 ± 12.1 | 86.0 ± 22.5 |
| 9th portion (in 120 min.) | 55.0 ± 12.0 | 77.0 ± 11.0 | 74.0 ± 12.0 | 88.0 ± 23.6 |

A comparative study of the effect of the present composition and that of histamine on acid-forming function of stomach mucosa in healthy volunteers has been carried out. For this purpose the characteristics of stomach acid-forming function were studied in these volunteers after administering said preparations in different sequences. The results are shown in Tables 23 and 24.

Tables 23 and 24 show that the present composition and histamine produce identical effects on stomach acid-forming function with respect to the duration and intensity of such effects. But the present composition is advantageous because it can be administered orally and produces no undesirable side-effects.

TABLE 23

The effect on the present composition and that of histamine on acid-forming function of stomach mucosa in healthy volunteers when histamine is administered in an hour after the present composition (a group of 11 volunteers).

| Characteristics of stomach-acid-forming function 1 | Basal secretion 2 | Stimulated with present compos. 3 |
|---|---|---|
| Total hydrochloric acid, meq./liter, M ± m | 1.07 ± 0.07 | 5.40 ± 0.09* |
| Free hydrochloric acid, | 1.20 ± 0.03 | 3.0 ± 0.08**) |

TABLE 23-continued

The effect on the present composition and that of histamine on acid-forming function of stomach mucosa in healthy volunteers when histamine is administered in an hour after the present composition (a group of 11 volunteers).

meq./liter, M ± m

| 1 | Secretion in interval bwn stimulators administration 4 | Histamine stimulated secretion 5 | Secretion in 1 h after histamine injection 6 |
|---|---|---|---|
| Total hydrochloric acid, meq/liter, M ± m | 32.4 ± 3.4*) | 4.70 ± 0.12*) | 4.6 ± 0.5*) |
| Free hydrochloric acid, meq/liter, M ± m | 21.7 ± 2.7**) | 3.90 ± 0.11**) | 6.92 ± 0.73**) |

Note:
*)means that the difference with basal secretion is true, p < 0.05;
**)means that the difference with basal secretion is true, p < 0.05.

TABLE 24

The effect of histamine and of the present composition on acid-forming function of stomach mucosa in healthy volunteers when the present composition is administered in an hour after histamine (a group of 11 volunteers)

| Characteristics of stomach acid-forming function 1 | Basal secretion 2 | Histamine secretion 3 |
|---|---|---|
| Total hydrochloric acid, meq./liter, M ± m | 2.80 ± 0.17 | 8.00 ± 0.29*) |
| Free hydrochloric acid, meq./liter, M ± m | 1.28 ± 0.14 | 6.5 ± 0.27**) |

| 1 | Secretion in interval bwn stimulators 4 | Present composition stimulated secretion 5 | Secretion in 1 h after present composition 6 |
|---|---|---|---|
| Total hydrochloric acid, meq./liter, M ± m | 15.8 ± 1.6*) | 10.5 ± 0.33*) | 5.8 ± 0.5*) |
| Free hydrochloric acid, meq./liter, M ± m | 15.3 ± 1.4**) | 6.60 ± 0.25**) | 0.27 ± 0.18**) |

Note:
*)means that the difference with basal secretion is true, p < 0.05;
**)means that the difference with basal secretion is true, p < 0.05.

The effect of the present composition on acid-forming function of stomach mucosa in patients suffering chronic alcoholism has been studied. A fractional study of gastric juice carried out in a clinic, showed that on the 3d day of alcohol abstinence syndrome acid-forming and secretory functions in patients were reduced significantly (gastric juice amounts in first portions were reduced to 2–5 ml), considerable amount of mucin was present. The administration of the present composition stimulated acid-forming function of stomach mucosa, caused increase in stomach contents amount, improved mucin secretion. The results of this study are shown in Table 25.

TABLE 25

The effect of the present composition on acid-forming function of stomach mucosa in patients suffering chronic alcoholism on the 3d day of alcohol abstinence syndrome (a group of 10 patients).

| Gastric juice portion, No. | Free hydrochloric acid, meq./l, M ± m | Total hydrochloric acid, meq./l, M ± m |
|---|---|---|
| 1st portion (0 min., basal secretion) | 0.85 ± 0.39 | 8.37 ± 1.70 |
| 2nd portion (in 15 min.) | 1.15 ± 0.39 | 11.60 ± 1.80 |
| 3d portion (in 30 min.) | 1.45 ± 0.38 | 11.50 ± 1.90 |
| 4th portion (in 45 min) | 2.35 ± 0.53 | 14.20 ± 3.00 |
| 5th portion (in 60 min.) | 1.40 ± 0.33 | 11.60 ± 1.90 |
| Stimulation with the present composition | | |
| 6th portion (in 15 min, stimulated secretion) | 4.70 ± 1.30 | 19.30 ± 3.30 |
| 7th portion (in 90 min.) | 6.80 ± 1.20 | 21.30 ± 3.30 |
| 8th portion (in 105 min.) | 4.59 ± 1.10 | 16.80 ± 1.80 |
| 9th portion (in 120 min.) | 1.40 ± 0.60 | 10.20 ± 1.90 |

When the same group of patients was treated with the present composition (total daily dosage of 8–12 mg/kg body weight), then by the end of the 1st day or by the beginning of the 2nd day these patients noted improved apepite, bitter tests disappeared, defecation normalized (constipation disappeared); and after 4–6 day os treatment with the present composition the acid-forming function of stomach mucosa was normalized (see Table 26).

TABLE 26

The effect of 4–6 days treatment with the present composition on acid-forming function of stomach mucosa in patients suffering chronic alcoholism at the stage of alcohol abstinence syndrome (a group of 10 patients).

| Gastric juice portion No. | Free hydrochloric acid, meq./l, M ± m | Total hydrochloric acid, meq./l. M ± m |
|---|---|---|
| 1st portion (0 min., basal secretion) | 5.96 ± 0.90 | 22.50 ± 1.30 |
| 2nd portion (in 15 min.) | 6.08 ± 0.90 | 23.10 ± 2.20 |
| 3d portion (in 30 min.) | 9.62 ± 1.10 | 24.10 ± 1.70 |
| 4th portion (in 45 min.) | 11.22 ± 1.20 | 27.40 ± 1.70 |
| 5th portion (in 60 min.) | 13.05 ± 0.93 | 31.70 ± 1.68 |
| Stimulation with the present composition | | |
| 6th portion (in 75 min., stimulated secretion) | 32.50 ± 3.00 | 59.90 ± 4.30 |
| 7th portion (in 90 min.) | 58.80 ± 5.20 | 89.90 ± 7.10 |
| 8th portion (in 105 min.) | 52.60 ± 5.00 | 83.30 ± 5.60 |
| 9th portion (in 120 min.) | 46.10 ± 5.00 | 76.50 ± 5.00 |

The fractional study of stomach contents in a group of ambulatory patients has shown that in the patients with worsened appetite the level of hydrochloric acid in gastric juice is somewhat reduced (see Table 27).

TABLE 27

The effect of the present composition on acid-forming function of stomach mucosa in ambulatory patients suffering chronic alcoholism (a group of 20 patients).

| Gustric juice portion No. | Free hydrochloric acid, meq./l, M ± m | Total hydrochloric acid, meq./l. M ± m |
|---|---|---|
| 1st portion, (0 min., basal secretion) | 3.52 ± 0.33 | 19.90 ± 0.89 |
| 2nd portion (in 15 min) | 4.02 ± 0.38 | 21.40 ± 0.78 |
| 3d portion (in 30 min.) | 4.71 ± 0.31 | 23.80 ± 0.66 |
| 4th portion (in 45 min.) | 4.94 ± 0.41 | 25.05 ± 0.53 |
| 5th portion (in 60 min.) | 4.52 ± 0.37 | 22.45 ± 0.42 |
| Stimulated with the present composition | | |
| 6th portion (in 75 min., stimulated secretion) | 8.95 ± 0.67 | 27.75 ± 0.48 |
| 7th portion (in 90 min.) | 10.70 ± 0.42 | 31.60 ± 0.60 |
| 8th portion (in 105 min.) | 11.70 ± 0.36 | 33.35 ± 0.36 |
| 9th portion (in 120 min.) | 12.30 ± 0.42 | 33.75 ± 0.78 |

When the same group of patients was treated with the present composition (a total daily dosage of 8–12 mg mg/kg of body weight), then on the 5th–7th day of treatment an increase in acid-forming activity of stomach mucosa was observed in all patients (see Table 28).

It should be noted that in ambulatory patients without such treatment no restoration of acid-forming function of stomach mucosa was observed within the above-mentioned period.

TABLE 28

The effect of 5–7 days treatment with the present composition on acid-forming function of stomach mucosa in ambulatory patients suffering chronic alcoholism (a group of 20 patients).

| Gastric juice portion No. | Free hydrochloric acid, meq./l, M ± m | Total hydrochloric acid, meq./l, M ± m |
|---|---|---|
| 1st portion (0 min., basal secretion) | 6.40 ± 0.57 | 22.65 ± 0.70 |
| 2nd portion (in 15 min.) | 6.99 ± 0.60 | 24.00 ± 0.96 |
| 3d portion (in 30 min.) | 10.44 ± 0.60 | 27.60 ± 1.10 |
| 4th portion (in 45 min.) | 9.00 ± 0.55 | 28.15 ± 1.68 |
| 5th portion (in 60 min.) | 5.90 ± 0.35 | 19.25 ± 1.02 |
| Stimulation with the present composition | | |
| 6th portion (in 75 min., stimulated secretion) | 21.35 ± 0.72 | 94.65 ± 2.10 |
| 7th portion (in 90 min.) | 53.85 ± 3.50 | 89.10 ± 5.90 |
| 8th portion (in 105 min.) | 43.05 ± 1.56 | 72.15 ± 3.00 |
| 9th portion (in 120 min.) | 44.60 ± 2.02 | 77.20 ± 4.20 |

Industrial Application

The present composition having antialcoholic activity, stimulating energy metabolism, acid-forming and secretory functions of stomach mucosa, having radioprotective and anticholera activity may be used in medicine as a drug for treating alcoholism, acute alcohol intoxication and its aftereffects, as a diagnisticum for determining acid-forming and secretory functions of stomach, for treating anacidic and hypoacidic gastrites, for treating hypotension, asthenic conditions, in particular those accompanying alcoholism and intensive physical exercises (in sport medicine, in different types of working activities), as a radioprotector for protecting against irradiation, and for preventing cholera.

We claim:

1. A pharmaceutical composition having activity for treating alcohol intoxication and alcohol abstinence syndrome consisting essentially of as active ingredients a mixture of succinic acid and citric acid or pharmaceutically acceptable salts thereof and a pharmaceutically acceptable solvent, diluent or carrier.

2. A pharmaceutical composition as in claim 1 in the form of solution or powder wherein said composition contains from 0.1 to 0.3 g of succinic acid and from 0.025 to 0.085 g of citric acid or pharmaceutically acceptable salts thereof per unit dose.

3. A pharmaceutical composition as in claim 1 wherein said pharmaceutical solvent is water or alkaline mineral water.

4. A method for preventing and treating alcohol intoxication and alcohol abstinence syndrome by administering orally to a mammal in need thereof an effective amount of the pharmaceutical composition according to claim 1 wherein the composition is administered separately from any alcohol.

5. A method according to claim 4 wherein the composition is administered in a dosage of 3.75 mg/kg of body weight.

6. The method according to claim 4 wherein the composition is administered prior to ingestion of alcohol.

7. A method according to claim 6 wherein the composition is administered in a dosage of 3.75 mg/kg of body weight.

8. A pharmaceutical composition in the form of a solution or a powder consisting essentially of from 0.1 to 0.3 grams of succinic acid and from 0.025 to 0.085 grams of citric acid or pharmaceutically acceptable salts thereof per unit dose and a pharmaceutically acceptable carrier, solvent or diluent.

9. The pharmaceutical composition according to claim 8 wherein the pharmaceutical solvent is water or alkaline mineral water.

* * * * *